United States Patent
Webster et al.

(10) Patent No.: US 8,544,766 B2
(45) Date of Patent: Oct. 1, 2013

(54) SCENT DISPENSER

(75) Inventors: William Webster, Portland, ME (US); David Gallant, Newfield, ME (US)

(73) Assignee: Novia Products LLC, Portland, ME (US)

( * ) Notice: Subject to any disclaimer, the term of this patent is extended or adjusted under 35 U.S.C. 154(b) by 605 days.

(21) Appl. No.: 12/814,005

(22) Filed: Jun. 11, 2010

(65) Prior Publication Data

US 2010/0314465 A1 Dec. 16, 2010

Related U.S. Application Data

(60) Provisional application No. 61/186,019, filed on Jun. 11, 2009.

(51) Int. Cl.
*A24F 25/00* (2006.01)

(52) U.S. Cl.
USPC ............... 239/34; 239/35; 239/36; 239/37; 239/50; 239/57

(58) Field of Classification Search
USPC ..................... 239/34–60; 222/251
See application file for complete search history.

(56) References Cited

U.S. PATENT DOCUMENTS

| | | | | | |
|---|---|---|---|---|---|
| 1,481,325 | A | * | 1/1924 | Le Gris | 239/55 |
| 2,234,062 | A | * | 3/1941 | Roberts | 63/1.15 |
| 2,763,395 | A | * | 9/1956 | Meek | 220/8 |
| 3,888,416 | A | * | 6/1975 | Lin | 239/34 |
| 4,200,229 | A | * | 4/1980 | Spector | 239/57 |
| 5,610,674 | A | | 3/1997 | Martin | |
| 5,898,475 | A | | 4/1999 | Martin | |
| 6,617,014 | B1 | | 9/2003 | Thomson | |
| 2002/0113909 | A1 | | 8/2002 | Sherwood | |
| 2007/0187524 | A1 | | 8/2007 | Sherwood | |
| 2007/0224232 | A1 | | 9/2007 | Sherwood | |

OTHER PUBLICATIONS www.scentair.com/products/index.php?subSectionID=2.
ScentWave SWD-1000 Technical Specifications.
ScentStream SXD-5020 Technical Specifications.
ScentPOP Technical Specifications.

* cited by examiner

*Primary Examiner* — Jason J Boeckmann
*Assistant Examiner* — Joel Zhou
(74) *Attorney, Agent, or Firm* — Greenberg Traurig, LLP

(57) ABSTRACT

An ambient environment modification mechanism such as a scent dispenser (which could also act as a filter) which may comprise a piston and a piston cylinder, receiving the piston, and forming a piston cylinder chamber volume when the piston is moved from an inserted position in the piston cylinder to a withdrawn position in the piston cylinder. The piston may have a hollow interior receiving an ambient air modification material holder, such as a cartridge, containing ambient air modification material. The hollow interior may be in fluid communication with the piston cylinder chamber volume at a first end of the hollow interior. A ventilation opening may be in fluid communication with the hollow interior at a second end of the hollow interior. A piston cylinder chamber volume forming mechanism, such as spring may move the piston relative to the piston cylinder from the inserted position to the withdrawn position.

4 Claims, 7 Drawing Sheets

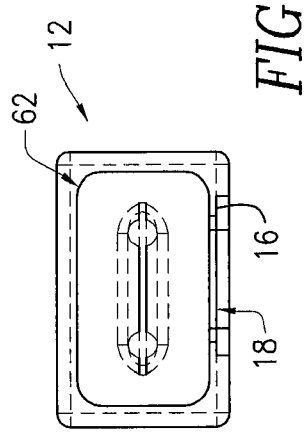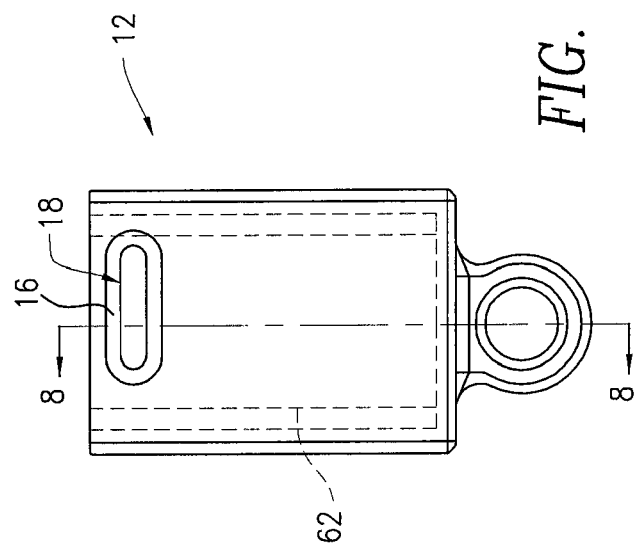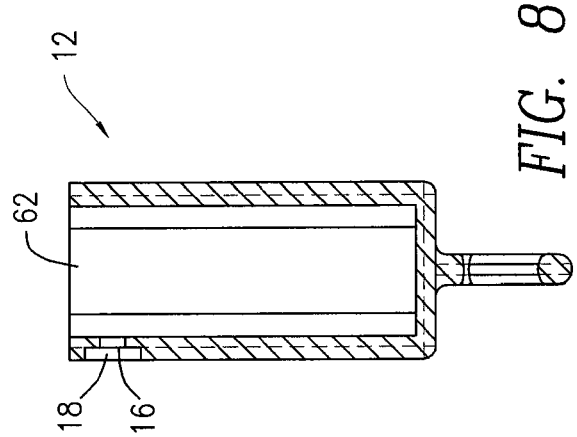

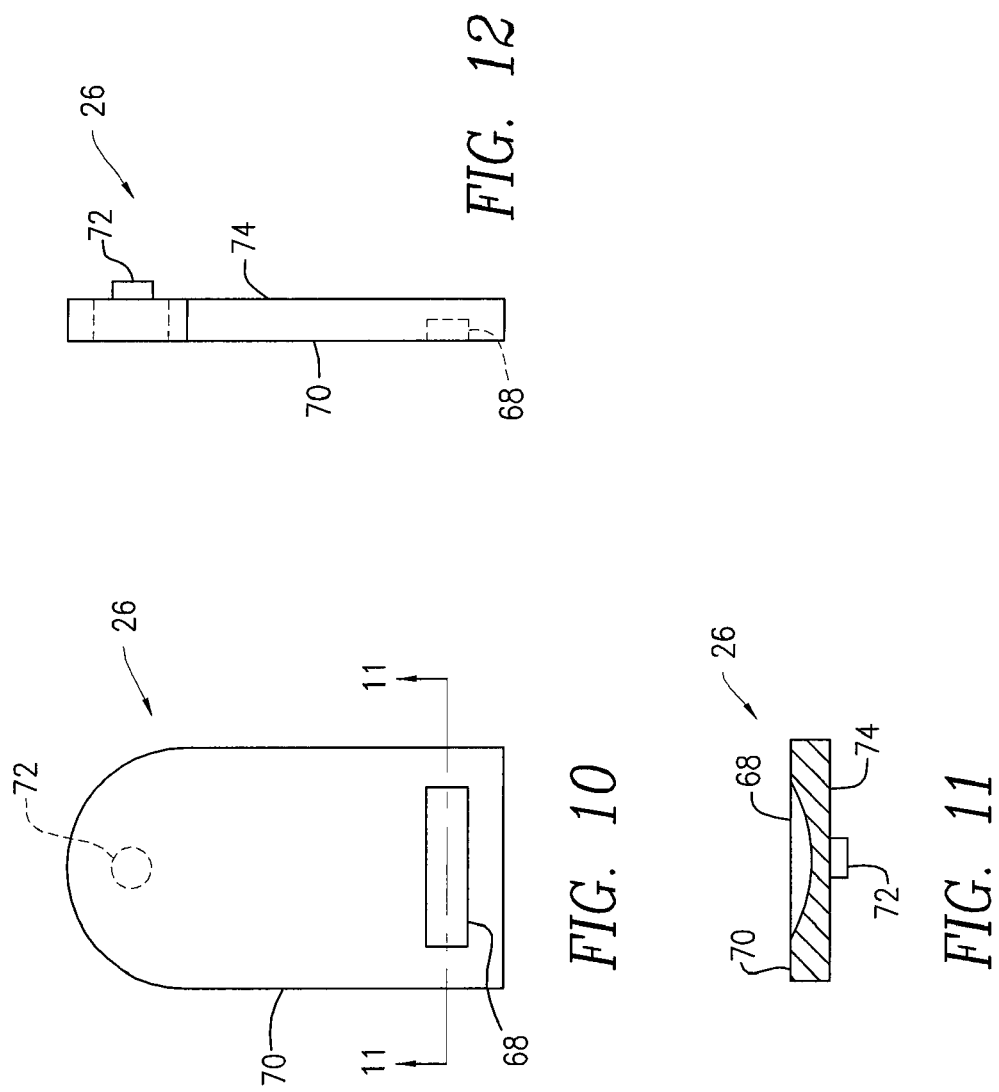

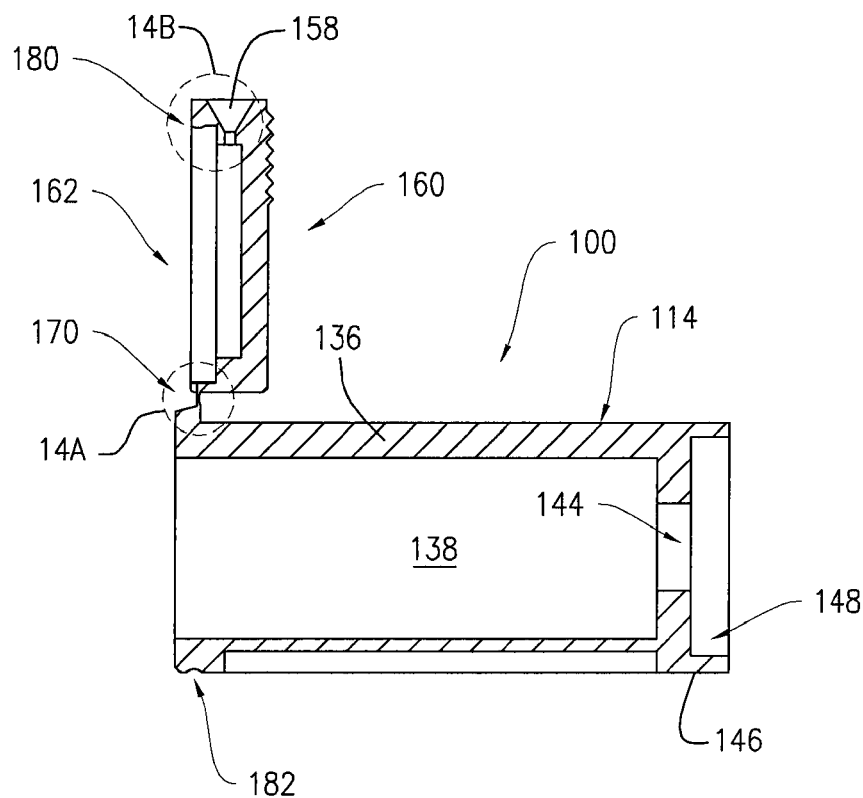
FIG. 14
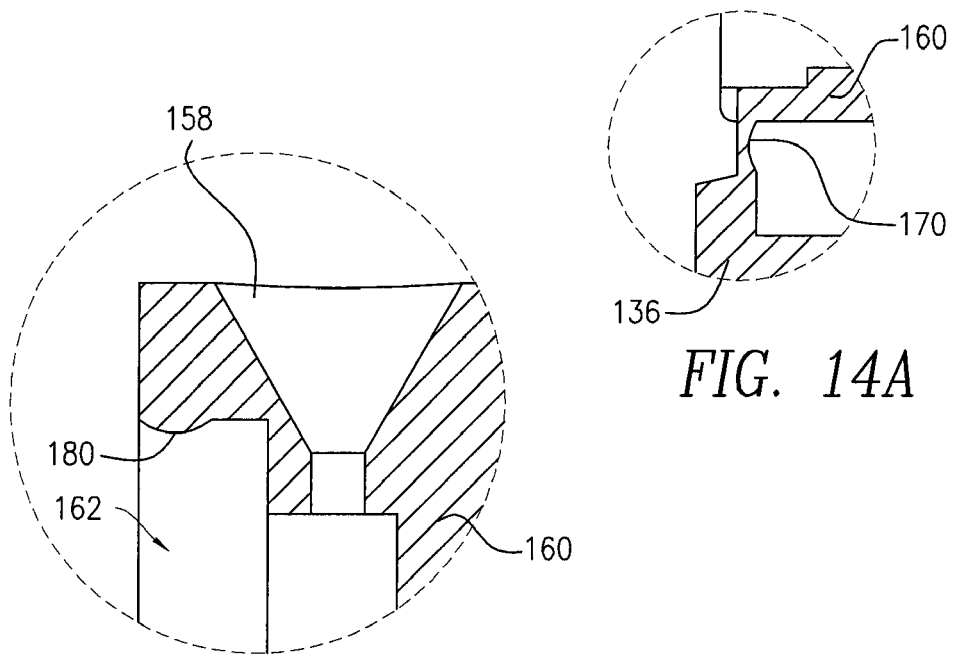
FIG. 14B
FIG. 14A

SCENT DISPENSER

CROSS REFERENCE TO RELATED APPLICATION

The present application claims priority to U.S. Provisional Application No. 61/186,019, entitled "SCENT DISPENSER" filed on Jun. 11, 2009, the disclosure of which is hereby incorporated by reference.

FIELD

The disclosed subject matter relates to dispensers of scents into the environment and/or absorbers of odors or materials from the environment.

BACKGROUND

Many forms of dispensers of scents into the environment, such as the household or other building interior environment, or devices for removing odors or materials from the environment, are known in the art. Applicants have improved the performance of such devices while maintaining simplicity and economics of manufacture and operation.

SUMMARY

According to one exemplary embodiment a scent dispenser comprises a cylinder defining a piston chamber for receiving a hollow piston. The piston includes a piston body that is closely fitted to the piston chamber, but may move upward and downward therein. The piston body defines a cartridge chamber that has openings through the piston body at both ends thereof and is adapted for receiving a scent cartridge having a scented core. The core includes a material that can reversibly absorb or adsorb a volatile scented substance and allows air to flow readily through the core. According to the exemplary embodiment the piston further includes a U-shaped flange at the top end of the piston body that has a groove for slidably receiving a door. The U-shaped flange, the groove and the door are arranged such that air flow through the opening at the top end of the piston body is blocked when the door is fully inserted into the U-shaped flange.

According to the exemplary embodiment the piston body and flange, together or separately, may also define a ventilation port arranged such that it provides the only path for air flow into or out of the cartridge chamber when the piston body is in the piston chamber and the door is inserted into the U-shaped flange into a blocking position. The cartridge chamber is in fluid communication with the piston cylinder chamber through the opening in the bottom of the piston body. An arrangement of a locking button and an L-shaped groove on the piston body provide means for releasing the piston for upward movement and for locking the piston in place when the piston body is fully inserted into the piston chamber. Motive force for the upward movement of the piston toward the locking position is provided by a spring in the piston chamber.

Upward movement of the piston causes suction to form in the piston cylinder chamber, drawing air into the piston cylinder chamber through the ventilation port and the cartridge chamber. A portion of the air passes through the scent cartridge, carrying some of the scented substance with it. Downward movement of the piston compresses the scented air in the piston cylinder chamber, forcing it through the cartridge chamber to be expelled through the ventilation port. A portion of the air from the piston cylinder chamber again passes through the scent cartridge, carrying away more of the scented material to be expelled through the ventilation port with the air.

BRIEF DESCRIPTION OF THE DRAWINGS

For a better understanding of the present invention, reference is made to the following detailed description of the exemplary embodiments considered in conjunction with the accompanying drawings, in which:

FIG. 7 is a front elevational view of the cylinder of the scent dispenser of FIG. 1;

FIG. 8 is a left elevational view of a cross-section of the cylinder of FIG. 7, taken at a vertical plane through the cylinder;

FIG. 9 is a top plan view of the cylinder of FIG. 7;

FIG. 10 is a top plan view of the door of the scent dispenser of FIG. 1;

FIG. 11 is a left elevational view of a cross-section of the door of FIG. 10, taken at a vertical plane through a fingernail slot recessed into the door;

FIG. 12 is a rear view of the door of FIG. 10, oriented such that the top of the door is at the left of the figure;

FIG. 14 is a cross-section view of the scent dispenser of FIG. 13 taken along the lines 14-14 in FIG. 13;

FIG. 14A is a close-up view of area 14A in FIG. 14;

FIG. 14B is a close-up view of area 14B in FIG. 14; and

DETAILED DESCRIPTION

Figure 1:
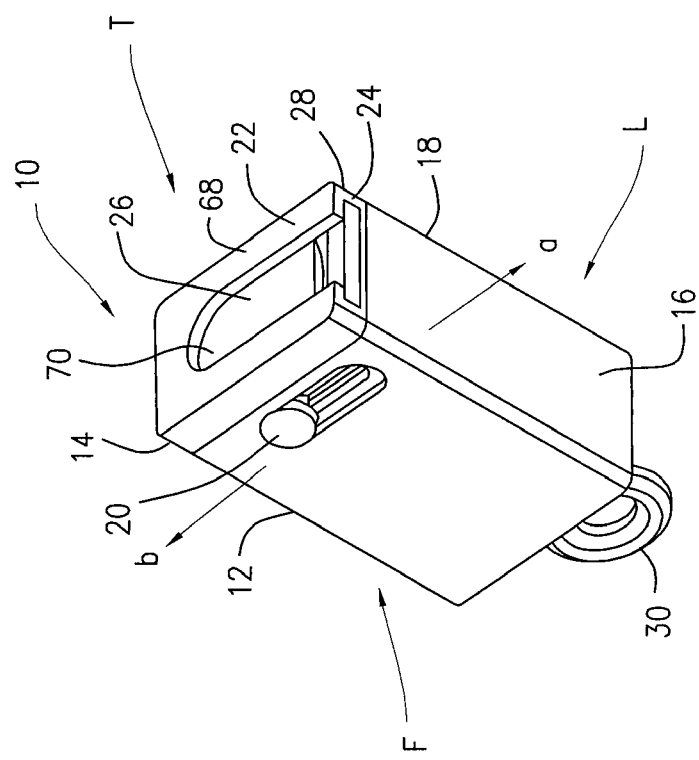
FIG. 1 is a perspective view of a scent dispenser according to an embodiment of the present invention.
Figure 2:
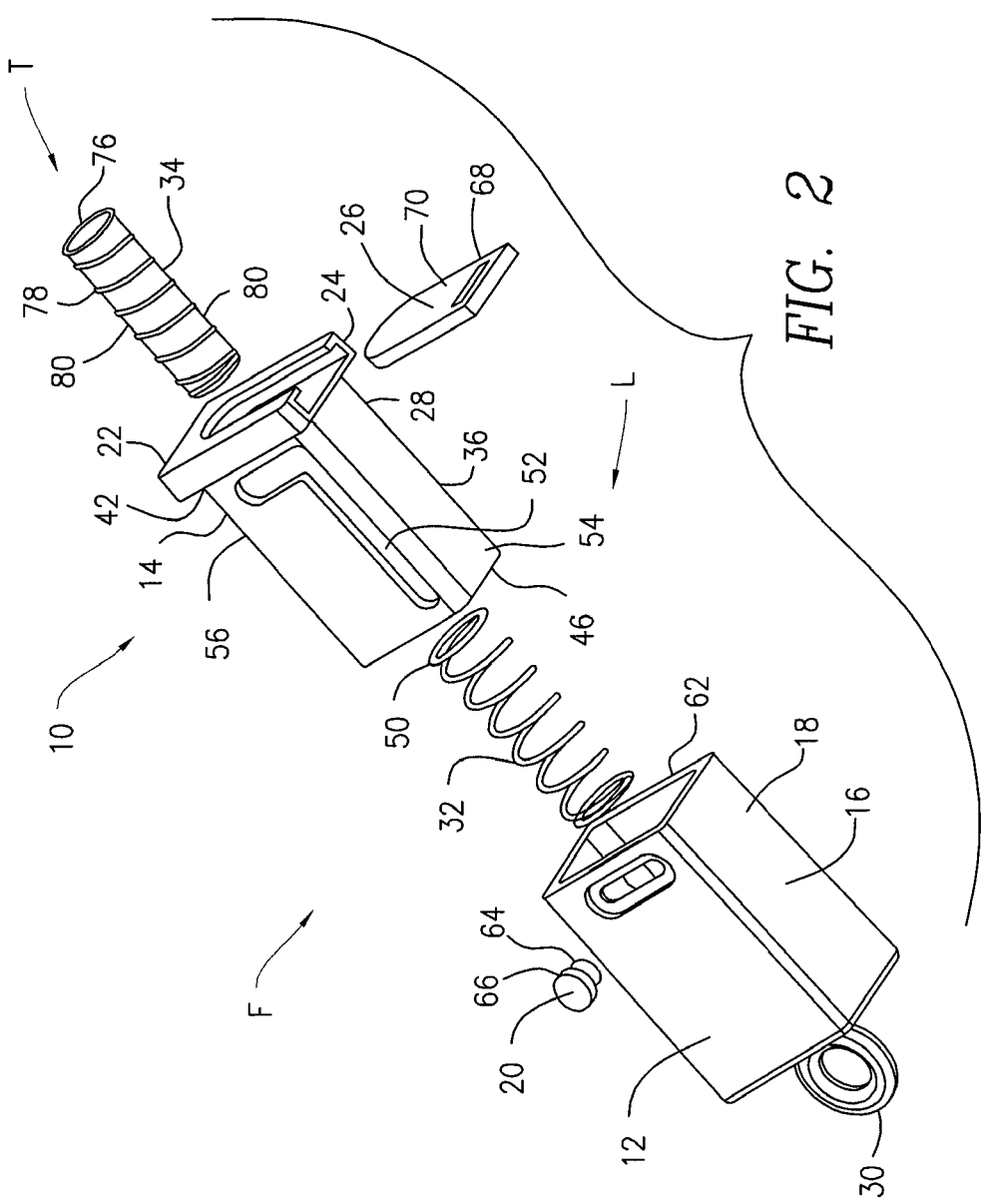
FIG. 2 is an exploded perspective view of the scent dispenser of FIG. 1.

FIGS. 1-12 present views of a scent dispenser 10 and its component parts according to embodiments. FIGS. 1 and 2 are perspective views of the scent dispenser 10 that illustrate relationships among various elements of the scent dispenser 10. However, consistent with the nature of perspective views, some elements of the scent dispenser 10 discussed herein are not visible in those figures. All such elements of the scent dispenser 10 are discussed further in relation to FIGS. 3-12, which present elevational, plan or cross-sectional views of certain component parts of the scent dispenser 10. Terms indicating position, orientation or direction of motion are used throughout the discussion of FIGS. 1-12 in relation to the component parts and are consistent with the orientation of the parts shown in FIGS. 1 and 2 unless otherwise expressly noted, or by default are in relation to the orientation within the illustration of the FIG. on the page. Such terms are used for the purpose of facilitating discussion, and not to limit the embodiments to the particular ones shown and described or to limit physical orientation in actual use to any particular coordinate system, such as horizontal, vertical and front, back and side while the device is in actual use.

FIG. 1 is a perspective view of the scent dispenser 10 in a fully-assembled and closed state. The scent dispenser 10 is oriented such that it may be viewed from the top direction "T", the front direction "F", and the left side direction "L". In regard to the direction of motion, "leftward" is the direction toward the left side of the scent dispenser 10 (i.e., the side indicated by "L") and is indicated by the arrow labeled "a". "Rightward" is the direction that is opposite to the leftward direction, and is indicated by the arrow labeled "b". The scent dispenser 10 includes a cylinder 12 arranged to receive a piston 14 such that the piston 14 may move upward or downward within the cylinder 12. The cylinder 12 defines a recessed ledge 16 and a slot 18, which are visible at the front of the scent dispenser 10. A lock button 20 resides in the slot 18 such that the lock button 20 may slide leftward or rightward within the slot 18. The lock button 20 will be discussed further below in the present application.

Figure 5:
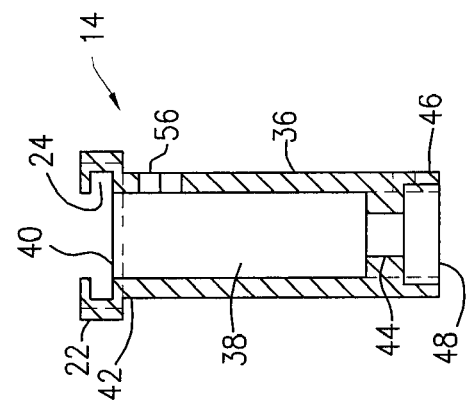
FIG. 5 is a right elevational view of a cross-section of the piston of FIG. 3, taken through a vertical plane through the piston.

Continuing to refer to FIG. 1, the piston 14 has a U-shaped flange 22, visible at the top of the scent dispenser 10, as seen more clearly in FIGS. 2 and 5 to possess such a U-shape in side view, which flange 22 defines a groove 24 that is arranged to receive a door 26 through the open end 28 of the "U" such that the door 26 fits closely within the groove 24 but may be moved leftward or rightward within the groove 24. In some embodiments, such as the illustrated embodiment, the piston 14 is arranged such that the U-shaped flange 22 contacts the cylinder 12 when the piston 14 is received to its maximum depth within the cylinder 12. A ring 30 that is attached to or integral with the cylinder 12 may optionally be provided, e.g. for the attachment of the dispenser 10 to another object, such as with a lanyard (not shown).

FIG. 2 is an exploded perspective view of the scent dispenser 10 of FIG. 1, showing additional elements of the scent dispenser 10 that are not visible in FIG. 1. The scent dispenser 10 of FIG. 2 is oriented such that it may be viewed from the top direction "T", the front direction "F", and the left side direction "L". As seen in FIG. 2, in addition to the elements discussed with respect to FIG. 1, the scent dispenser 10 includes a spring 32 and a scent cartridge 34. The spring 32 and scent cartridge 34 will be discussed further below in the present application.

Figure 6:
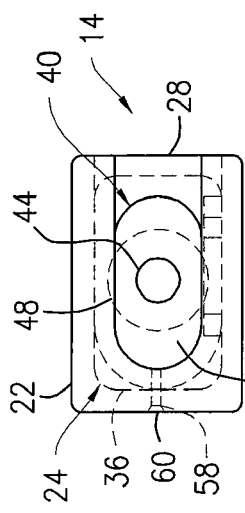
FIG. 6 is a top plan view of the piston of FIG. 3.
Figure 3:
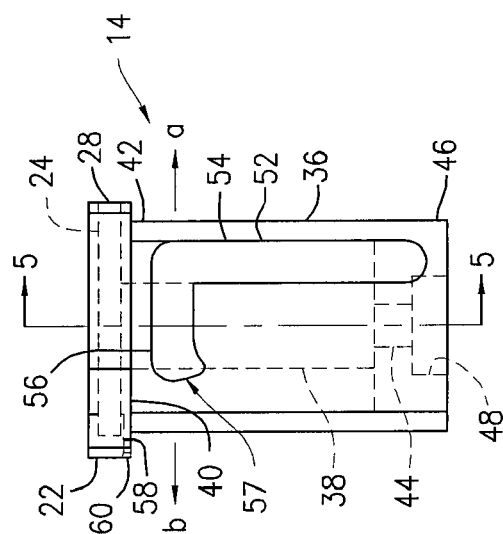
FIG. 3 is a front elevational view of the piston of the scent dispenser of FIG. 1.
Figure 4:
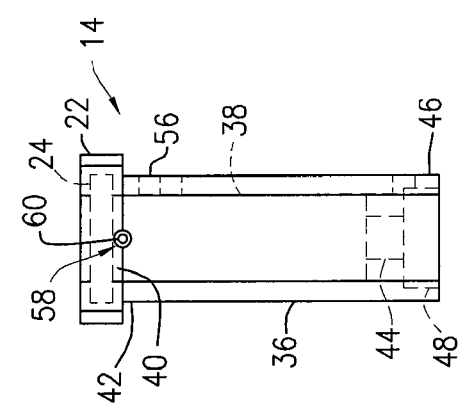
FIG. 4 is a right elevational view of the piston of FIG. 3.
Figure 13:
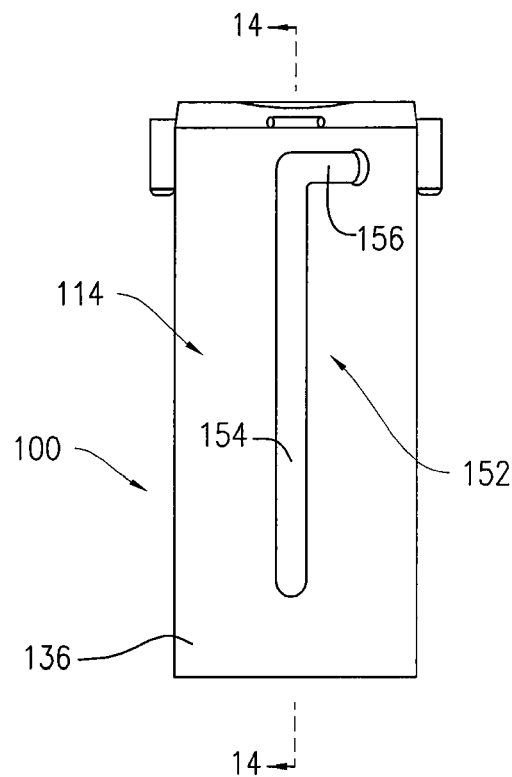
FIG. 13 is a side view of a scent dispenser according to another embodiment.
Figure 15:
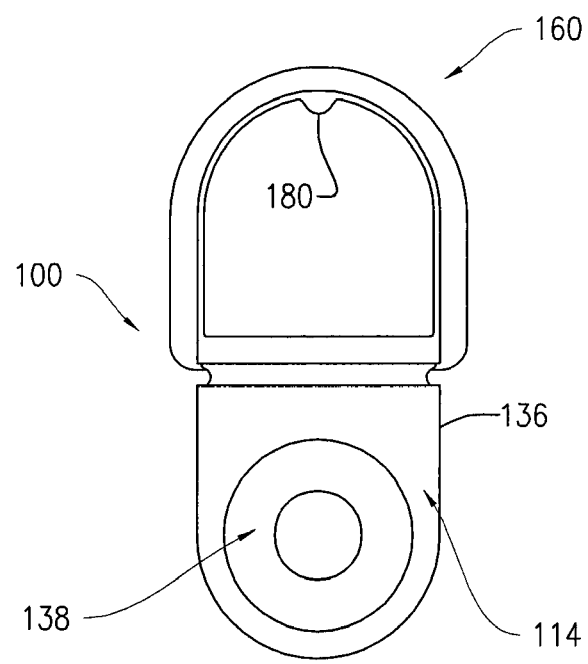
FIG. 15 is a top view of the scent dispenser of FIG. 13.

FIGS. 3-6 present elevational, plan and cross-sectional views of the piston 14, of which FIG. 3 is a front elevational view, FIG. 4 is a right elevational view, FIG. 5 is a right elevational cross-sectional view, taken through a vertical plane through the piston 14, along lines 5-5 shown in FIG. 4, and FIG. 6 is a top plan view. Terms indicating position, orientation or direction of motion of the piston 14 or its elements are defined in relation to the front elevational view of the piston 14 in FIG. 3, and thus are consistent with their usage with respect to FIGS. 1 and 2. In regard to the direction of motion, "leftward" is the direction toward the left side of the scent dispenser 10 (i.e., the side indicated by "L") and is indicated by the arrow labeled "a". "Rightward" is the direction that is opposite to the leftward direction, and is indicated by the arrow labeled "b". To understand the elements and function of the piston 14, FIGS. 3-6 should be read together and in conjunction with FIGS. 1 and 2.

Referring to FIGS. 3-6 in conjunction with FIGS. 1 and 2, the piston 14 has a cylindrical piston body 36, which is attached to or integral with the U-shaped flange 22. The piston body 36 is partially hollow and defines a cartridge chamber 38 arranged such that the scent cartridge 34 may be received entirely within the cartridge chamber 38. The piston body 36 also defines an opening 40 through the top end 42 of the piston body 36 which is arranged to allow passage of the scent cartridge 34 into or out of the cartridge chamber 38. The piston body 36 also defines an opening 44 at the bottom end 46 of the piston body 36 which is arranged to prevent passage of the scent cartridge 34 out of the cartridge chamber 38 while providing fluid communication between the cartridge chamber 38 and the environment of the piston body 36, i.e., into the piston cylinder chamber volume formed as the piston 14 is withdrawn from the cylinder 12. In some embodiments, such as the illustrated embodiment, the piston body 36 also defines a receiving bore 48 at the bottom end 46 of the piston body 36 that is arranged to securely receive an end 50 of the spring 32. In some embodiments, such as the illustrated embodiment, the receiving bore 48 also provides fluid communication between the cartridge chamber 38 and the interior of the piston 12, through the opening 44.

Continuing to refer to FIGS. 3-6 in conjunction with FIGS. 1 and 2, the piston 14 is provided with an L-shaped groove 52 that is recessed into the piston body 36 and has a vertical leg 54 and a transverse leg 56. The L-shaped groove 52 is arranged such that its vertical leg 54 is oriented along the direction of travel of the piston 14 within the cylinder 12 and has a length equal to the distance over which the piston 14 is desired to travel. The L-shaped groove 52 is further arranged such that its transverse leg 56 is oriented to coincide with the slot 18 of the cylinder 12 when the piston body 36 is at its furthest limit of downward travel within the cylinder 12. In some embodiments, such as the illustrated embodiment, the transverse leg 56 has a notch 57 at its end furthest from the vertical leg 54. The notch 57 is arranged to receive the lock button 20 such that pressure must be applied to the lock button 20 to dislodge it from the notch 57. The L-shaped groove 52 is further arranged to further receive the lock button 20 in a manner that is discussed below in the present application.

Continuing to refer to FIGS. 3-6 in conjunction with FIGS. 1 and 2, the U-shaped flange 22 is arranged such as to completely expose the opening 40. The U-shaped flange 22 and the groove 24 are further arranged such that the door 26 may fit snugly within the groove 24 such as to completely cover the opening 40, thus preventing air flow through the opening 40. The U-shaped flange 22 is further arranged such that it is larger in at least one horizontal direction than the top end 42 of the piston body 36. In the illustrated embodiment, the U-shaped flange 22 is larger than the top end 42 in all horizontal directions.

Continuing to refer to FIGS. 3-6 in conjunction with FIGS. 1 and 2, the piston body 36 and U-shaped flange 22 define a ventilation port 58 that provides fluid communication between the cartridge chamber 38 and the environment of the scent dispenser 10. The ventilation port 58 is positioned below the groove 24 such that the passage of air through the ventilation port 58 is not impeded by the door 26 when the door 26 is fully inserted into the U-shaped flange 22. In some embodiments, such as the illustrated embodiment, the ventilation port 58 is defined by the piston body 36 and the U-shaped flange 22 such that fluid communication between the cartridge chamber 38 and the environment of the scent dispenser 10 is not blocked when the piston 14 is at its furthest limit of downward travel within the cylinder 12. In other embodiments, the ventilation port 58 may be entirely defined by the U-shaped flange 22. Other forms of ventilation opening may be envisioned, including one for within or partly by the door 26 in position to block most air flow into the piston chamber 38, but allowing smaller flow associated with a ventilation opening 58 as discussed above.

In some embodiments, such as the illustrated embodiment, the ventilation port 58 is formed opposite the open end 28 of the U-shaped flange. In other embodiments, the ventilation port 58 is formed at some other position along the U-shaped flange. In some embodiments, the ventilation port 58 has an effective diameter of 1 mm or less. In some embodiments, such as the illustrated embodiment, the ventilation port 58 is provided with a counterbore 60 that flares outward toward the environment such as to reduce resistance of air flow into the cartridge chamber 38 through the ventilation port 58 and to aid the dispersal of scent passing out of the cartridge chamber 38 through the ventilation port 58. Air flow into and out of the cartridge chamber 38 occurs through the operation of the scent dispenser 10 as discussed below in the present application.

FIGS. 7-9 present elevational, plan and cross-sectional views of the cylinder 12, of which FIG. 7 is a front elevational view, FIG. 8 is a left elevational cross-sectional view taken at a vertical plane through the cylinder 12, along lines 8-8 in FIG. 7, and FIG. 9 is a top plan view. Terms indicating position, orientation or direction of motion of the cylinder 12 or its elements are defined in relation to the front elevational view of the cylinder 12 in FIG. 7, and thus are consistent with their usage with respect to FIGS. 1 and 2. To understand the elements and function of the cylinder 12, FIGS. 7-9 should be read together and in conjunction with FIGS. 1 and 2.

Referring to FIGS. 7-9 in conjunction with FIGS. 1 and 2, the cylinder 12 defines a cylindrical piston chamber 62 that is arranged to receive the piston body 36 such that the piston body 36 fits closely within the piston chamber 62 while allowing the piston body 36 to move readily upward or downward therein. The slot 18 penetrates the cylinder 12 such that the piston body 36 is exposed through the slot 18.

Referring to FIG. 2 in conjunction with FIGS. 3-7, the lock button 20 has a small end 64 that is arranged to reside in the slot 18 and a large end 66 that is arranged to reside on the recessed ledge 16. The lock button 20 is further arranged such that the small end 64 may extend through the slot 18 into the L-shaped groove 52 of the piston 14 when the large end 66 resides on the recessed ledge 16. In such an arrangement, the lock button 20 prevents the upward or downward movement of the piston 14 when the lock button 20 resides in the transverse leg 56 of the L-shaped groove 52 and allows the upward or downward movement of the piston 14 when it resides in the vertical leg 54 of the L-shaped groove 52. The slot 18 and L-shaped groove 52 are arranged such that, when the piston body 36 is at its furthest limit of downward travel into the cylinder 12, the lock button 20 may be moved from the vertical leg 54 to the transverse leg 56, or vice versa, by sliding the lock button 20 within the slot 18 leftward or rightward, as appropriate.

FIGS. 10-12 present elevational, plan and cross-sectional views of the door 26, of which FIG. 10 is a top plan view, FIG. 11 is a left elevational cross-sectional view taken at a vertical plane through a finger slot 68 recessed into a top surface 70 of the door 26, taken along lines 11-11 in FIG. 10, and FIG. 12 is a rear view, oriented such that the top surface 70 of the door 26 is at the left of FIG. 12. Terms indicating position, orientation or direction of motion of the door 26 or its elements are defined such as to be consistent with similar terms used in relation to FIGS. 1-6. To understand the elements and function of the door 26, FIGS. 10-12 should be read together and in conjunction with FIGS. 1-6.

Referring to FIGS. 10-12 in conjunction with FIGS. 1-6, in some embodiments, such as the illustrated embodiment, the door 26 is provided with a fingernail slot 68 recessed into a top surface 70 of the door 26, which may be used to conveniently move the door 26 rightward and leftward (as defined in the discussions of FIGS. 1 and 3) within the groove 24 of the U-shaped flange 22. In some embodiments, the fingernail slot 68 is arranged such as to conveniently receive the edge of a fingernail or of a small coin. The door 26 is also provided with a stub 72 that protrudes from a bottom surface 74 of the door 26. The stub 72 is arranged on the door 26 such that, with the door 26 within the groove 18 of the U-shaped flange 22, the stub 72 protrudes into the opening 40 of the cartridge chamber 38. The stub 72 protrudes into the opening 40 such that leftward movement of the door 26 is limited by contact between the stub 72 and the piston body 36 preventing the door 26 from being readily removed from the U-shaped flange 22. The stub 72 is further arranged on the door 26 such that, at the limit of its leftward movement, the door 26 exposes enough of the opening 40 that the scent cartridge 34 may readily pass through the opening 40 into or out of the cartridge chamber 38. In some embodiments, the stub 72 can be attached to a threaded member threaded engaging the door such that in one position the threaded member and stud are not extending beyond either side of the door 26. When the threaded portion is threaded into an opening shown in phantom in FIG. 12. In other embodiments, the stub 72 may be the end of a screw or tack entering the top surface 70 and protruding through the bottom surface 74.

Referring to FIG. 2 in conjunction with FIGS. 3-6, the spring 32 is arranged to fit within the piston chamber 62 in contact with bottom end 46 of the piston body 36. In some embodiments, such as the illustrated embodiment, the end 50 of the spring 32 is secured in the receiving bore 48 of the piston body 36 such as to center the spring 32 within the piston chamber 62. The spring 48 exerts an upward force on the piston 14 such that the piston 14 moves upward without being pulled. In some embodiments, such as the illustrated embodiment, the spring 32 is a helical compression spring.

Referring to FIG. 2, the scent cartridge 34 includes a core 76 that can absorb and/or adsorb a volatile scented substance and allows the ready passage of air through the core 76. In some embodiments, such as the illustrated embodiment, the scent cartridge 34 includes a frame, such as spring 78, that provides structural support to the core 76 and helps to maintain its shape. In some embodiments, such as the illustrated embodiment, the frame has open gaps 80 through which air may flow. The core 76 contains an amount of a volatile scented substance, such as those used in perfumes, for attracting game, as diet aids, for aroma therapy, for medical applications, or for other uses which are known or may become known. In some embodiments, the core 76 is arranged such that the scented substance may be added directly to the core 76 to replenish or change the scent.

The core 76 may be made of any material that can carry and release volatile scented substances. In some embodiments of the invention, the core 50 is made of an absorbent fibrous material or closed cell foam having air passages penetrating there through. In other embodiments of the invention, the core 50 is made of an open-cell foam that presents an appreciable ratio of surface area to volume of foam, with higher ratios typically being preferred. In such embodiments of the invention, the foam may be a hydrophilic foam or have a hydrophilic material exposed at the surfaces of the cells. In some such embodiments, the core 50 comprises an open-cell foam composite made of a substantially hydrophobic foam to provide structure to the composite and a substantially hydrophilic foam exposed at the surfaces of the cells. An example of such a foam is described in U.S. Pat. No. 6,617,014.

The various elements of the scent dispenser 10 are arranged such that, when the scent dispenser 10 is fully assembled, the ventilation port 58 provides the only path by which air may move into or out of the scent dispenser 10. The fully-assembled scent dispenser 10 may be operated in the manner described herein with reference to FIGS. 1 and 2. Beginning in the closed state shown in FIG. 1, the lock button 20 is moved leftward (i.e., in the direction indicated by the arrow labeled "a" in FIGS. 1 and 3) within the slot 18 such that the small end 64 of the lock button 20 enters the vertical leg 54 of the L-shaped groove 52. This action frees the piston 14 to travel upward, with the motive force provided by the spring 32. As the piston 14 travels upward, suction is created within the piston cylinder chamber 62, drawing air into the confined piston cylinder chamber volume formed as the piston 14 is withdrawn through the piston cylinder chamber 62, through the ventilation port 58 and the cartridge chamber 38. As the air is drawn in, some or all of the air passes through the scent cartridge 34, carrying some of the volatile scented material into the piston cylinder chamber 62.

After the piston 14 has traveled upward for some distance, it may be pressed downward into the cylinder 12, such as by a user applying pressure to the piston 14 to counteract the spring force of spring 32. Such action causes the air in the piston chamber 62 to become compressed, forcing air to pass from the piston cylinder chamber 62 through the cartridge chamber 38, to be expelled through the ventilation port 58. Some or all of the air again passes through the scent cartridge 34, carrying away an additional amount of the volatile scented material which is expelled with the air through the ventilation port 58. The further the travel of the piston 14, the more air, and scent, is expelled. When the piston 14 is fully inserted into the cylinder 12, the lock button 20 may be moved rightward (i.e., in the direction indicated by the arrow labeled "b" in FIGS. 1 and 3) into the transverse leg 56 of the L-shaped groove 52, preventing upward movement of the piston 14. Other mechanical or electromechanical mechanisms (not shown) may be utilized to move the piston 14 in the direction in which air is expelled from the piston cylinder chamber 62 volume returning through the scent cartridge 34 and out the ventilation opening 58.

During operation of the scent dispenser 10, the door 26 remains fully-inserted into the groove 24 of the U-shaped flange 22, thus blocking air flow through the opening 40 of the cartridge chamber 38. When the scent dispenser 10 is not being operated, the door 26 may be moved leftward (i.e., in the direction indicated by the arrow labeled "a" in FIGS. 1 and 3) to expose the opening 40 such that the scent cartridge 34 may be removed or replaced, or that scented material may be added to its core 76.

Turning now to FIGS. 13, 14, 14A, 14B and 15 there is illustrated a scent dispenser 100, which, unless indicated otherwise, includes the features mentioned above with respect to the scent dispenser 10. The scent dispenser 100, which may be made from a suitable plastic material, such as poly-vinyl chloride, includes a piston 114 having a piston body 136. The piston body 136 includes a hollow interior forming a cylindrical cartridge chamber 138 with a bottom opening 144 (see FIG. 14). The piston body 136 includes a bottom end 146 with a hollow opening forming a spring receiving bore 148 (see FIG. 14). The exterior of the piston 114 is formed with an L-shaped grove 152 having a vertical leg 154 and a horizontal leg 156 (see FIG. 13), which are sized and shaped similar to and function the same as the vertical leg 54 and the horizontal leg 56 of the scent dispenser 10 of FIGS. 1-12.

The scent dispenser 100 includes a hinged top 160, with a hollow interior 162 and a ventilation opening 158 formed in a side wall of the hollow interior 162. The hinged top 160 is connected to the piston body 136 by a hinge 170. FIG. 14A is a close up of the area 14A in FIG. 14. The hinged top 160 may be formed with a snap lock protrusion 180, which may engage a detent groove 182 on the exterior wall of the piston body 136 (see FIG. 14). FIG. 14B is a close up view of the area 14B in FIG. 14 showing the snap lock protrusion 180.

In operation, the scent dispenser 100 operates similarly to the scent dispenser 10 illustrated in FIGS. 1-12, with the exception of the hinged top 160 replacing the door 26 in function, and the ventilation opening 58 is formed in the hinged top 160 in fluid communication with the cartridge chamber 138. The piston 114 is inserted into a piston cylinder (not shown in FIGS. 13, 14, 14A, 14B and 15) having a circular cylinder opening (not shown) to receive the piston 114 in relatively sealing engagement (although a seal such as an o-ring may also be used) and sucks in ambient air through the scent dispenser 100 cartridge (not shown in FIGS. 13, 14, 14A, 14B and 15) as the piston 114 is moved to a withdrawn position. The air is then pushed out the ventilation opening 158 when the piston 114 is moved in the opposite direction to an inserted position, again passing through the cartridge (not shown) on the way out.

It should be understood that the embodiments discussed herein are merely exemplary and that a person skilled in the relevant arts may make many variations and modifications thereto without departing from the spirit and scope of the invention. For example, in the illustrated embodiment, the cylinder 12, piston body 36 and piston chamber 62 substantially have the shape of a cylinder having a rectangular horizontal cross-section. In other embodiments, corresponding elements may be provided as cylinders having other horizontal cross-sectional shapes, such as a circular cross-section, an elliptical cross-section, or a non-rectangular polygonal cross-section. In embodiments having a circular cross-section, the ledge 16, slot 18 and lock button 20 may be replaced by an element, such as a screw, that is secured to the cylinder and protrudes into the interior of the cylinder such as to engage an L-shaped groove in the piston body that corresponds to the L-shaped groove 52 of the piston body 36. The piston body may then be released to move upward by rotating the piston, in the manner of opening a bayonet lock, such that the protruding element moves into the vertical leg of the L-shaped groove, allowing the piston to move upward. In some such embodiments, the rest of the operation of the scent dispenser would be the same as has been described above with respect to scent dispenser 10.

In some embodiments, the scent dispenser may be equipped with a seal, such as an o-ring seal on the outside of the body of the piston 14 near the bottom end 46 to facilitate the formation of the suction effect as the piston 14 moves within the cylinder 12 to form the confined piston cylinder chamber volume, as discussed above. The cylinder 12 may also be of cylindrical shape, as opposed to the rectangular cylinder shape of the disclosed exemplary embodiment.

Further, the scent dispenser of the disclosed exemplary embodiment may serve as an odor or other toxicant-carrying material remover. The scent cartridge 38, instead of carrying material desired to be released into the atmosphere for the provision of some pleasing aroma or masking of some undesirable aroma, may capture and remove from the environment undesired particulate or other materials causing an undesired aroma or other undesirable conditions in the ambient environment air. By acting as a particulate filter for particulate carried in the ambient atmosphere passed through the cartridge 34 according to the operation of the exemplary embodiment discussed in the present application, the scent dispenser 10 can also act to modify the ambient environment of the air around the dispenser 10.

It will be understood by those skilled in the art that an ambient environment modification mechanism is disclosed by way of example as a scent dispenser (which could also act as a filter) which may comprise the piston 14 and the piston cylinder 12, receiving the piston 14, and forming a piston cylinder chamber volume when the piston 14 is moved from an inserted position in the piston cylinder 12 to a withdrawn position in the piston cylinder 12. The inserted position may be any point of insertion up to full insertion and the withdrawn position may be any point short of full withdrawal, which full withdrawal would break the air seal between ambient and the piston cylinder chamber volume. The piston 14 may have a hollow interior 38 receiving an ambient air modification material holder, such as the cartridge 34, containing ambient air modification material, such as to emit material to generate a pleasing aroma in the ambient environment air or mask an undesired aroma in the ambient air or such as to filter particles adversely effecting the ambient environment air. The hollow interior 38 may be in fluid communication with the piston cylinder chamber volume at a first end of the hollow interior 38. A ventilation opening such as ventilation port 58 may be in fluid communication with the hollow interior 28 at a second end of the hollow interior 38. A piston cylinder 12 chamber volume forming mechanism, such as spring 32 may move the piston 14 relative to the piston cylinder 12 from the inserted position to the withdrawn position.

What is claimed is:

1. A scent dispenser, comprising: a piston cylinder having a sidewall and a pair of opposed ends, one of which is closed and the other of which is open, said sidewall surrounding an interior of said piston cylinder; a piston positioned in said piston cylinder for reciprocating movement relative thereto between a depressed position and an extended position, said piston including an imperforate peripheral wall surrounding an internal chamber which is in pneumatic communication with said interior of said piston cylinder, a first open end and a second open end opposite said first open end, said second open end of said piston being mounted within said interior of said piston cylinder and being positioned proximate said one end of said piston cylinder when said piston is in its said depressed position and distal from said one end of said piston cylinder when said piston is in its said extended position, and said first open end of said piston being positioned proximate said other end of said piston cylinder when said piston is in its said depressed position and distal from said other end of said piston cylinder when said piston is in its said extended position; a cover for closing said first open end of said piston; a ventilation port located proximate said first open end of said piston, said ventilation port being in pneumatic communication with said internal chamber of said piston and with the atmosphere when said piston is in its said depressed position and in its said extended position; an ambient air modification material received within said internal chamber of said piston; and urging means for urging said piston from its said depressed position into its said extended position, whereby air is drawn from the atmosphere into said scent dispenser through said ventilation port, then through said ambient air modification material into said interior of said piston cylinder, and wherein movement of said piston from its extended position to its depressed position forces air from said interior of said piston cylinder through said ambient air modification material then through said ventilation port to the atmosphere, a position-limiting mechanism for limiting movement of said piston, said position-limiting mechanism including a projecting member projecting from said sidewall of said piston cylinder toward said piston and a first groove in the external surface of said peripheral wall of said piston for slidably receiving said projecting member such that said first groove guides said piston toward its extended position with said projecting member slidably received in said first groove, said first groove having an end arranged to catch said projecting member so as to stop movement of said piston at its extended position.

2. The scent dispenser of claim 1, further comprising a locking mechanism for retaining said piston in its depressed position, said locking mechanism including a second groove in said external surface of said peripheral wall of said piston for slidably receiving said projecting member, said second groove extending from said first groove at an angle thereto and located proximate said first open end of said piston such that said projecting member is slidably received in said second groove when said piston is in its depressed position.

3. The scent dispenser of claim 1, wherein said ventilation port penetrates said cover.

4. The scent dispenser of claim 1, wherein said cover is movable between a closed position in which said first open end of said piston is substantially blocked by said cover and an open position in which said ambient air modification material is removable from said internal chamber of said piston through said first open end thereof.

* * * * *